United States Patent
Cunningham

(10) Patent No.: US 8,257,387 B2
(45) Date of Patent: Sep. 4, 2012

(54) METHOD OF TRANSFERRING PRESSURE IN AN ARTICULATING SURGICAL INSTRUMENT

(75) Inventor: James S. Cunningham, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 609 days.

(21) Appl. No.: 12/192,243

(22) Filed: Aug. 15, 2008

(65) Prior Publication Data

US 2010/0042140 A1    Feb. 18, 2010

(51) Int. Cl.
*A61B 17/00* (2006.01)
(52) U.S. Cl. .................................................. 606/206
(58) Field of Classification Search .................. 606/205, 606/207
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,459,187 A | 3/1967 | Pallotta |
| 3,372,288 A | 3/1968 | Wigington |
| 3,643,663 A | 2/1972 | Sutter |

(Continued)

FOREIGN PATENT DOCUMENTS

CA    2104423    2/1994

(Continued)

OTHER PUBLICATIONS

EPO translation of DE10031773.*

(Continued)

*Primary Examiner* — Gary Jackson
*Assistant Examiner* — Amy Shipley

(57) ABSTRACT

An end effector for a surgical instrument includes a fixed bearing member with mounting surfaces for attachment to a distal end of the surgical instrument. At least one jaw member of the end effector is configured to move relative to an opposing jaw member between open and closed configurations, and a force transfer member is configured for longitudinal motion with respect to the fixed bearing member. The force transfer member includes a pivot channel therein. The end effector also includes a reactive member coupled between the fixed bearing member and the at least one jaw member. The reactive member is constructed from a thin strip of conformable material and extends through the pivot channel such that relative longitudinal motion between the fixed bearing member and the force transfer member causes the reactive member to flex and the at least one jaw member to move relative to the opposing jaw.

15 Claims, 7 Drawing Sheets

U.S. PATENT DOCUMENTS

| | | |
|---|---|---|
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,880 A | 1/1995 | Hooven |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |

| | | | | | | |
|---|---|---|---|---|---|---|
| 5,422,567 A | 6/1995 | Matsunaga | | 5,611,813 A | 3/1997 | Lichtman |
| 5,423,810 A | 6/1995 | Goble et al. | | 5,620,415 A | 4/1997 | Lucey et al. |
| 5,425,690 A | 6/1995 | Chang | | 5,620,453 A | 4/1997 | Nallakrishnan |
| 5,425,739 A | 6/1995 | Jessen | | 5,620,459 A | 4/1997 | Lichtman |
| 5,429,616 A | 7/1995 | Schaffer | | 5,624,452 A | 4/1997 | Yates |
| 5,431,672 A | 7/1995 | Cote et al. | | 5,626,578 A | 5/1997 | Tihon |
| 5,431,674 A | 7/1995 | Basile et al. | | 5,626,609 A | 5/1997 | Zvenyatsky et al. |
| 5,437,292 A | 8/1995 | Kipshidze et al. | | 5,630,833 A | 5/1997 | Katsaros et al. |
| 5,438,302 A | 8/1995 | Goble | | 5,637,110 A | 6/1997 | Pennybacker et al. |
| 5,439,478 A | 8/1995 | Palmer | | 5,638,003 A | 6/1997 | Hall |
| 5,441,517 A | 8/1995 | Kensey et al. | | 5,638,827 A * | 6/1997 | Palmer et al. .................. 600/564 |
| 5,443,463 A | 8/1995 | Stern et al. | | 5,643,294 A | 7/1997 | Tovey et al. |
| 5,443,464 A | 8/1995 | Russell et al. | | 5,647,869 A | 7/1997 | Goble et al. |
| 5,443,479 A * | 8/1995 | Bressi, Jr. ...................... 606/205 | | 5,647,871 A | 7/1997 | Levine et al. |
| 5,443,480 A | 8/1995 | Jacobs et al. | | 5,649,959 A | 7/1997 | Hannam et al. |
| 5,445,638 A | 8/1995 | Rydell et al. | | 5,655,650 A | 8/1997 | Naitou |
| 5,445,658 A | 8/1995 | Durrfeld et al. | | 5,658,281 A | 8/1997 | Heard |
| 5,449,480 A | 9/1995 | Kuriya et al. | | D384,413 S | 9/1997 | Zlock et al. |
| 5,451,224 A | 9/1995 | Goble et al. | | 5,662,667 A | 9/1997 | Knodel |
| 5,454,823 A | 10/1995 | Richardson et al. | | 5,665,100 A | 9/1997 | Yoon |
| 5,454,827 A | 10/1995 | Aust et al. | | 5,667,526 A | 9/1997 | Levin |
| 5,456,684 A | 10/1995 | Schmidt et al. | | 5,674,220 A | 10/1997 | Fox et al. |
| 5,458,598 A | 10/1995 | Feinberg et al. | | 5,674,229 A | 10/1997 | Tovey et al. |
| 5,460,629 A | 10/1995 | Shlain et al. | | 5,681,282 A | 10/1997 | Eggers et al. |
| 5,461,765 A | 10/1995 | Linden et al. | | 5,688,270 A | 11/1997 | Yates et al. |
| 5,462,546 A | 10/1995 | Rydell | | 5,690,652 A | 11/1997 | Wurster et al. |
| 5,472,442 A | 12/1995 | Klicek | | 5,690,653 A | 11/1997 | Richardson et al. |
| 5,472,443 A | 12/1995 | Cordis et al. | | 5,693,051 A | 12/1997 | Schulze et al. |
| 5,476,479 A * | 12/1995 | Green et al. ................. 606/205 | | 5,693,920 A | 12/1997 | Maeda |
| 5,478,351 A | 12/1995 | Meade et al. | | 5,695,522 A | 12/1997 | LeMaire, III et al. |
| 5,480,406 A | 1/1996 | Nolan et al. | | 5,700,261 A | 12/1997 | Brinkerhoff |
| 5,480,409 A | 1/1996 | Riza | | 5,700,270 A | 12/1997 | Peyser et al. |
| 5,484,436 A | 1/1996 | Eggers et al. | | 5,702,390 A | 12/1997 | Austin et al. |
| 5,496,312 A | 3/1996 | Klicek | | 5,707,369 A | 1/1998 | Vaitekunas et al. |
| 5,496,317 A | 3/1996 | Goble et al. | | 5,709,680 A | 1/1998 | Yates et al. |
| 5,496,347 A | 3/1996 | Hashiguchi et al. | | 5,716,366 A | 2/1998 | Yates |
| 5,499,997 A | 3/1996 | Sharpe et al. | | 5,720,744 A | 2/1998 | Eggleston et al. |
| 5,509,922 A | 4/1996 | Aranyi et al. | | 5,722,421 A | 3/1998 | Francese et al. |
| 5,512,721 A | 4/1996 | Young et al. | | 5,725,536 A | 3/1998 | Oberlin et al. |
| 5,514,134 A | 5/1996 | Rydell et al. | | 5,727,428 A | 3/1998 | LeMaire, III et al. |
| 5,527,313 A | 6/1996 | Scott et al. | | 5,735,848 A | 4/1998 | Yates et al. |
| 5,528,833 A | 6/1996 | Sakuma | | 5,743,906 A | 4/1998 | Parins et al. |
| 5,529,067 A | 6/1996 | Larsen et al. | | 5,752,973 A | 5/1998 | Kieturakis |
| 5,531,744 A | 7/1996 | Nardella et al. | | 5,755,717 A | 5/1998 | Yates et al. |
| 5,536,251 A | 7/1996 | Evard et al. | | 5,759,188 A | 6/1998 | Yoon |
| 5,540,684 A | 7/1996 | Hassler, Jr. | | 5,766,130 A | 6/1998 | Selmonosky |
| 5,540,685 A | 7/1996 | Parins et al. | | 5,766,166 A | 6/1998 | Hooven |
| 5,540,706 A | 7/1996 | Aust et al. | | 5,766,170 A | 6/1998 | Eggers |
| 5,540,715 A | 7/1996 | Katsaros et al. | | 5,766,196 A | 6/1998 | Griffiths |
| 5,542,945 A | 8/1996 | Fritzsch | | 5,769,849 A | 6/1998 | Eggers |
| 5,558,671 A | 9/1996 | Yates | | 5,772,655 A | 6/1998 | Bauer et al. |
| 5,558,672 A | 9/1996 | Edwards et al. | | 5,772,670 A | 6/1998 | Brosa |
| 5,562,619 A | 10/1996 | Mirarchi et al. | | 5,776,128 A | 7/1998 | Eggers |
| 5,562,699 A | 10/1996 | Heimberger et al. | | 5,776,130 A | 7/1998 | Buysse et al. |
| 5,562,720 A | 10/1996 | Stern et al. | | 5,779,646 A | 7/1998 | Koblish et al. |
| 5,564,615 A | 10/1996 | Bishop et al. | | 5,779,701 A | 7/1998 | McBrayer et al. |
| 5,569,241 A | 10/1996 | Edwards | | H1745 H | 8/1998 | Paraschac |
| 5,569,243 A | 10/1996 | Kortenbach et al. | | 5,792,137 A | 8/1998 | Carr et al. |
| 5,571,100 A | 11/1996 | Goble et al. | | 5,792,165 A | 8/1998 | Klieman et al. |
| 5,573,424 A | 11/1996 | Poppe | | 5,792,177 A | 8/1998 | Kaseda |
| 5,573,534 A | 11/1996 | Stone | | 5,797,537 A | 8/1998 | Oberlin et al. |
| 5,573,535 A | 11/1996 | Viklund | | 5,797,927 A | 8/1998 | Yoon |
| 5,575,799 A | 11/1996 | Bolanos et al. | | 5,797,938 A | 8/1998 | Paraschac et al. |
| 5,575,805 A | 11/1996 | Li | | 5,797,941 A | 8/1998 | Schulze et al. |
| 5,578,052 A | 11/1996 | Koros et al. | | 5,797,958 A | 8/1998 | Yoon |
| 5,579,781 A | 12/1996 | Cooke | | 5,797,959 A * | 8/1998 | Castro et al. .................. 606/207 |
| 5,582,611 A | 12/1996 | Tsukagoshi et al. | | 5,800,449 A | 9/1998 | Wales |
| 5,582,617 A | 12/1996 | Klieman et al. | | 5,807,393 A | 9/1998 | Williamson, IV et al. |
| 5,585,896 A | 12/1996 | Yamazaki et al. | | 5,810,764 A | 9/1998 | Eggers et al. |
| 5,590,570 A | 1/1997 | LeMaire, III et al. | | 5,810,805 A | 9/1998 | Sutcu et al. |
| 5,591,181 A | 1/1997 | Stone et al. | | 5,810,808 A | 9/1998 | Eggers |
| 5,597,107 A | 1/1997 | Knodel et al. | | 5,810,811 A | 9/1998 | Yates et al. |
| 5,601,224 A | 2/1997 | Bishop et al. | | 5,810,877 A | 9/1998 | Roth et al. |
| 5,601,601 A | 2/1997 | Tal et al. | | 5,814,043 A | 9/1998 | Shapeton |
| 5,601,641 A | 2/1997 | Stephens | | 5,814,054 A | 9/1998 | Kortenbach et al. |
| 5,603,711 A | 2/1997 | Parins et al. | | 5,817,093 A | 10/1998 | Williamson, IV et al. |
| 5,603,723 A | 2/1997 | Aranyi et al. | | 5,817,119 A | 10/1998 | Klieman et al. |
| 5,611,798 A | 3/1997 | Eggers | | 5,820,630 A | 10/1998 | Lind |
| 5,611,808 A | 3/1997 | Hossain et al. | | 5,824,978 A | 10/1998 | Karasik et al. |

| | | | | | | |
|---|---|---|---|---|---|---|
| 5,827,271 A | 10/1998 | Buysse et al. | 6,090,107 A | 7/2000 | Borgmeier et al. | |
| 5,827,279 A | 10/1998 | Hughett et al. | 6,096,037 A | 8/2000 | Mulier et al. | |
| 5,827,281 A | 10/1998 | Levin | 6,099,550 A | 8/2000 | Yoon | |
| 5,827,323 A | 10/1998 | Klieman et al. | 6,102,909 A | 8/2000 | Chen et al. | |
| 5,827,548 A | 10/1998 | Lavallee et al. | 6,106,542 A | 8/2000 | Toybin et al. | |
| 5,833,690 A | 11/1998 | Yates et al. | 6,110,171 A | 8/2000 | Rydell | |
| 5,843,080 A | 12/1998 | Fleenor et al. | 6,113,596 A | 9/2000 | Hooven et al. | |
| 5,849,022 A | 12/1998 | Sakashita et al. | 6,113,598 A | 9/2000 | Baker | |
| 5,853,412 A | 12/1998 | Mayenberger | 6,117,158 A | 9/2000 | Measamer et al. | |
| 5,859,527 A | 1/1999 | Cook | 6,122,549 A | 9/2000 | Sharkey et al. | |
| 5,860,976 A | 1/1999 | Billings et al. | 6,123,701 A | 9/2000 | Nezhat | |
| 5,876,401 A | 3/1999 | Schulze et al. | H1904 H | 10/2000 | Yates et al. | |
| 5,876,412 A | 3/1999 | Piraka | 6,126,658 A | 10/2000 | Baker | |
| 5,882,567 A | 3/1999 | Cavallaro et al. | 6,126,665 A | 10/2000 | Yoon | |
| 5,891,141 A | 4/1999 | Rydell | 6,139,563 A | 10/2000 | Cosgrove, III et al. | |
| 5,891,142 A | 4/1999 | Eggers et al. | 6,143,005 A | 11/2000 | Yoon et al. | |
| 5,893,863 A | 4/1999 | Yoon | 6,152,923 A | 11/2000 | Ryan | |
| 5,893,875 A | 4/1999 | O'Connor et al. | 6,162,220 A | 12/2000 | Nezhat | |
| 5,893,877 A | 4/1999 | Gampp, Jr. et al. | 6,171,316 B1 | 1/2001 | Kovac et al. | |
| 5,897,563 A | 4/1999 | Yoon et al. | 6,174,309 B1 | 1/2001 | Wrublewski et al. | |
| 5,902,301 A | 5/1999 | Olig | 6,178,628 B1 | 1/2001 | Clemens et al. | |
| 5,906,630 A | 5/1999 | Anderhub et al. | 6,179,834 B1 | 1/2001 | Buysse et al. | |
| 5,908,420 A | 6/1999 | Parins et al. | 6,179,837 B1 | 1/2001 | Hooven | |
| 5,908,432 A | 6/1999 | Pan | 6,183,467 B1 | 2/2001 | Shapeton et al. | |
| 5,911,719 A | 6/1999 | Eggers | 6,187,003 B1 | 2/2001 | Buysse et al. | |
| 5,913,874 A | 6/1999 | Berns et al. | 6,190,386 B1 | 2/2001 | Rydell | |
| 5,921,916 A | 7/1999 | Aeikens et al. | 6,190,399 B1 * | 2/2001 | Palmer et al. | 606/205 |
| 5,921,984 A | 7/1999 | Sutcu et al. | 6,190,400 B1 | 2/2001 | Vandemoer et al. | |
| 5,925,043 A | 7/1999 | Kumar et al. | 6,193,718 B1 | 2/2001 | Kortenbach et al. | |
| 5,928,136 A | 7/1999 | Barry | 6,206,876 B1 | 3/2001 | Levine et al. | |
| 5,935,126 A | 8/1999 | Riza | 6,206,877 B1 | 3/2001 | Kese et al. | |
| 5,941,869 A | 8/1999 | Patterson et al. | 6,206,893 B1 | 3/2001 | Klein et al. | |
| 5,944,718 A | 8/1999 | Dafforn et al. | 6,214,028 B1 | 4/2001 | Yoon et al. | |
| 5,951,546 A | 9/1999 | Lorentzen | 6,217,602 B1 | 4/2001 | Redmon | |
| 5,951,549 A | 9/1999 | Richardson et al. | 6,217,615 B1 | 4/2001 | Sioshansi et al. | |
| 5,954,720 A | 9/1999 | Wilson et al. | 6,221,039 B1 | 4/2001 | Durgin et al. | |
| 5,954,731 A | 9/1999 | Yoon | 6,223,100 B1 | 4/2001 | Green | |
| 5,954,733 A | 9/1999 | Yoon | 6,224,593 B1 | 5/2001 | Ryan et al. | |
| 5,957,923 A | 9/1999 | Hahnen et al. | 6,224,614 B1 | 5/2001 | Yoon | |
| 5,957,937 A | 9/1999 | Yoon | 6,228,080 B1 | 5/2001 | Gines | |
| 5,960,544 A | 10/1999 | Beyers | 6,228,083 B1 | 5/2001 | Lands et al. | |
| 5,961,514 A | 10/1999 | Long et al. | 6,248,124 B1 | 6/2001 | Pedros et al. | |
| 5,964,758 A | 10/1999 | Dresden | 6,248,944 B1 | 6/2001 | Ito | |
| 5,967,997 A * | 10/1999 | Turturro et al. | 600/567 | 6,261,307 B1 | 7/2001 | Yoon et al. | |
| 5,976,132 A | 11/1999 | Morris | 6,267,761 B1 | 7/2001 | Ryan | |
| 5,984,932 A | 11/1999 | Yoon | 6,270,497 B1 | 8/2001 | Sekino et al. | |
| 5,984,938 A | 11/1999 | Yoon | 6,270,508 B1 | 8/2001 | Klieman et al. | |
| 5,984,939 A | 11/1999 | Yoon | 6,273,887 B1 | 8/2001 | Yamauchi et al. | |
| 5,989,277 A | 11/1999 | LeMaire, III et al. | 6,277,117 B1 | 8/2001 | Tetzlaff et al. | |
| 5,993,466 A | 11/1999 | Yoon | 6,280,458 B1 | 8/2001 | Boche et al. | |
| 5,993,467 A | 11/1999 | Yoon | 6,283,961 B1 | 9/2001 | Underwood et al. | |
| 5,997,565 A | 12/1999 | Inoue | D449,886 S | 10/2001 | Tetzlaff et al. | |
| 6,004,332 A | 12/1999 | Yoon et al. | 6,298,550 B1 | 10/2001 | Kirwan | |
| 6,004,335 A | 12/1999 | Vaitekunas et al. | 6,302,424 B1 | 10/2001 | Gisinger et al. | |
| 6,010,516 A | 1/2000 | Hulka et al. | 6,319,262 B1 | 11/2001 | Bates et al. | |
| 6,017,358 A | 1/2000 | Yoon et al. | 6,319,451 B1 | 11/2001 | Brune | |
| 6,021,693 A | 2/2000 | Feng-Sing | 6,322,561 B1 | 11/2001 | Eggers et al. | |
| 6,024,741 A | 2/2000 | Williamson et al. | 6,322,580 B1 | 11/2001 | Kanner | |
| 6,024,743 A | 2/2000 | Edwards | 6,325,795 B1 | 12/2001 | Lindemann et al. | |
| 6,024,744 A | 2/2000 | Kese et al. | 6,334,860 B1 | 1/2002 | Dorn | |
| 6,027,522 A | 2/2000 | Palmer | 6,334,861 B1 | 1/2002 | Chandler et al. | |
| 6,030,384 A | 2/2000 | Nezhat | 6,345,532 B1 | 2/2002 | Coudray et al. | |
| 6,033,399 A | 3/2000 | Gines | 6,350,264 B1 | 2/2002 | Hooven | |
| 6,039,733 A | 3/2000 | Buysse et al. | 6,352,536 B1 | 3/2002 | Buysse et al. | |
| 6,041,679 A | 3/2000 | Slater et al. | 6,358,249 B1 | 3/2002 | Chen et al. | |
| 6,050,996 A | 4/2000 | Schmaltz et al. | 6,358,259 B1 | 3/2002 | Swain et al. | |
| 6,053,914 A | 4/2000 | Eggers et al. | 6,358,268 B1 | 3/2002 | Hunt et al. | |
| 6,053,933 A | 4/2000 | Balazs et al. | 6,364,879 B1 | 4/2002 | Chen et al. | |
| D424,694 S | 5/2000 | Tetzlaff et al. | D457,958 S | 5/2002 | Dycus et al. | |
| D425,201 S | 5/2000 | Tetzlaff et al. | D457,959 S | 5/2002 | Tetzlaff et al. | |
| 6,059,782 A | 5/2000 | Novak et al. | 6,387,094 B1 | 5/2002 | Eitenmuller | |
| 6,066,139 A | 5/2000 | Ryan et al. | 6,391,035 B1 | 5/2002 | Appleby et al. | |
| 6,074,386 A | 6/2000 | Goble et al. | 6,398,779 B1 | 6/2002 | Buysse et al. | |
| 6,077,287 A | 6/2000 | Taylor et al. | 6,402,747 B1 | 6/2002 | Lindemann et al. | |
| 6,080,180 A | 6/2000 | Yoon et al. | 6,409,728 B1 | 6/2002 | Ehr et al. | |
| RE36,795 E | 7/2000 | Rydell | H2037 H | 7/2002 | Yates et al. | |
| 6,083,223 A | 7/2000 | Baker | 6,419,675 B1 | 7/2002 | Gallo, Sr. | |
| 6,086,586 A | 7/2000 | Hooven | 6,425,896 B1 | 7/2002 | Baltschun et al. | |
| 6,086,601 A | 7/2000 | Yoon | 6,432,112 B2 | 8/2002 | Brock et al. | |

| Patent No. | Date | Inventor(s) |
|---|---|---|
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | de Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |

| Patent Number | Date | Inventor(s) | Publication Number | Date | Inventor(s) |
|---|---|---|---|---|---|
| 7,156,842 B2 | 1/2007 | Sartor et al. | 2003/0158548 A1 | 8/2003 | Phan et al. |
| 7,156,846 B2 | 1/2007 | Dycus et al. | 2003/0158549 A1 | 8/2003 | Swanson |
| 7,160,298 B2 | 1/2007 | Lawes et al. | 2003/0171747 A1 | 9/2003 | Kanehira et al. |
| 7,160,299 B2 | 1/2007 | Baily | 2003/0181910 A1 | 9/2003 | Dycus et al. |
| 7,169,146 B2 | 1/2007 | Truckai et al. | 2003/0216732 A1 | 11/2003 | Truckai et al. |
| 7,179,255 B2 | 2/2007 | Lettice et al. | 2003/0220637 A1 | 11/2003 | Truckai et al. |
| 7,179,258 B2 | 2/2007 | Buysse et al. | 2003/0229344 A1 | 12/2003 | Dycus et al. |
| 7,195,631 B2 | 3/2007 | Dumbauld | 2003/0236325 A1 | 12/2003 | Bonora |
| D541,418 S | 4/2007 | Schechter et al. | 2003/0236518 A1 | 12/2003 | Marchitto et al. |
| 7,207,990 B2 | 4/2007 | Lands et al. | 2004/0030330 A1 | 2/2004 | Brassell et al. |
| D541,938 S | 5/2007 | Kerr et al | 2004/0030332 A1 | 2/2004 | Knowlton et al. |
| 7,223,264 B2 | 5/2007 | Daniel et al. | 2004/0049185 A1 | 3/2004 | Latterell et al. |
| 7,223,265 B2 | 5/2007 | Keppel | 2004/0064151 A1 | 4/2004 | Mollenauer |
| 7,232,440 B2 | 6/2007 | Dumbauld et al. | 2004/0073238 A1 | 4/2004 | Makower |
| 7,241,288 B2 | 7/2007 | Braun | 2004/0073256 A1 | 4/2004 | Marchitto et al. |
| 7,241,296 B2 | 7/2007 | Buysse et al. | 2004/0078035 A1 | 4/2004 | Kanehira et al. |
| 7,244,257 B2 | 7/2007 | Podhjahsky et al. | 2004/0082952 A1 | 4/2004 | Dycus et al. |
| 7,246,734 B2 | 7/2007 | Shelto, IV | 2004/0087943 A1 | 5/2004 | Dycus et al. |
| 7,248,944 B2 | 7/2007 | Green | 2004/0115296 A1 | 6/2004 | Duffin |
| 7,252,667 B2 | 8/2007 | Moses et al. | 2004/0116924 A1 | 6/2004 | Dycus et al. |
| 7,255,697 B2 | 8/2007 | Dycus et al. | 2004/0116979 A1 | 6/2004 | Truckai et al. |
| 7,267,677 B2 | 9/2007 | Johnson et al. | 2004/0143263 A1 | 7/2004 | Schechter et al. |
| 7,270,660 B2 | 9/2007 | Ryan | 2004/0148035 A1 | 7/2004 | Barrett et al. |
| 7,270,664 B2 | 9/2007 | Johnson et al. | 2004/0162557 A1 | 8/2004 | Tetzlaff et al. |
| 7,276,068 B2 | 10/2007 | Johnson et al. | 2004/0193153 A1 | 9/2004 | Sartor et al. |
| 7,300,435 B2 | 11/2007 | Wham et al. | 2004/0199181 A1 | 10/2004 | Knodel et al. |
| 7,303,557 B2 | 12/2007 | Wham et al. | 2004/0210282 A1 | 10/2004 | Flock et al. |
| 7,311,709 B2 | 12/2007 | Truckai et al. | 2004/0224590 A1 | 11/2004 | Rawa et al. |
| 7,314,471 B2 | 1/2008 | Holman | 2004/0230189 A1 | 11/2004 | Keppel |
| 7,318,823 B2 | 1/2008 | Sharps et al. | 2004/0236326 A1 | 11/2004 | Schulze et al. |
| 7,329,256 B2 | 2/2008 | Johnson et al. | 2004/0243125 A1 | 12/2004 | Dycus et al. |
| 7,329,257 B2 | 2/2008 | Kanehira et al. | 2004/0249374 A1 | 12/2004 | Tetzlaff et al. |
| D564,662 S | 3/2008 | Moses et al. | 2004/0260281 A1 | 12/2004 | Baxter, III et al. |
| 7,338,526 B2 | 3/2008 | Steinberg | 2005/0004564 A1 | 1/2005 | Wham et al. |
| 7,342,754 B2 | 3/2008 | Fitzgerald et al. | 2005/0004569 A1 | 1/2005 | Witt et al. |
| 7,344,268 B2 | 3/2008 | Jhigamian | 2005/0033278 A1 | 2/2005 | McClurken et al. |
| D567,943 S | 4/2008 | Moses et al. | 2005/0059934 A1 | 3/2005 | Wenchell et al. |
| 7,367,976 B2 | 5/2008 | Lawes et al. | 2005/0096645 A1 | 5/2005 | Wellman et al. |
| 7,377,920 B2 | 5/2008 | Buysse et al. | 2005/0101951 A1 | 5/2005 | Wham et al. |
| 7,384,420 B2 | 6/2008 | Dycus et al. | 2005/0101952 A1 | 5/2005 | Lands et al. |
| 7,384,421 B2 | 6/2008 | Hushka | 2005/0113818 A1 | 5/2005 | Sartor et al. |
| 7,396,336 B2 | 7/2008 | Orszulak et al. | 2005/0113819 A1 | 5/2005 | Wham et al. |
| D575,395 S | 8/2008 | Hushka | 2005/0113826 A1 | 5/2005 | Johnson et al. |
| D575,401 S | 8/2008 | Hixson et al. | 2005/0149017 A1 | 7/2005 | Dycus |
| 7,435,249 B2 | 10/2008 | Buysse et al. | 2005/0149151 A1 | 7/2005 | Orszulak et al. |
| 7,442,193 B2 | 10/2008 | Shields et al. | 2005/0154387 A1 | 7/2005 | Moses et al. |
| 7,442,194 B2 | 10/2008 | Dumbauld et al. | 2005/0187547 A1 | 8/2005 | Sugi |
| 7,445,621 B2 | 11/2008 | Dumbauld et al. | 2005/0197659 A1 | 9/2005 | Bahney |
| 7,458,972 B2 | 12/2008 | Keppel | 2005/0203504 A1 | 9/2005 | Wham et al. |
| 7,473,253 B2 | 1/2009 | Dycus et al. | 2006/0052778 A1 | 3/2006 | Chapman et al. |
| 7,481,810 B2 | 1/2009 | Dumbauld et al. | 2006/0052779 A1 | 3/2006 | Hammill |
| 7,487,780 B2 | 2/2009 | Hooven | 2006/0064085 A1 | 3/2006 | Schechter et al. |
| 7,491,201 B2 | 2/2009 | Shields et al. | 2006/0064086 A1 | 3/2006 | Odom |
| 7,491,202 B2 | 2/2009 | Odom et al. | 2006/0074417 A1 | 4/2006 | Cunningham et al. |
| 7,500,975 B2 | 3/2009 | Cunningham et al. | 2006/0079888 A1 | 4/2006 | Mulier et al. |
| 7,510,556 B2 | 3/2009 | Nguyen et al. | 2006/0079890 A1 | 4/2006 | Guerra |
| 7,513,898 B2 | 4/2009 | Johnson et al. | 2006/0079891 A1 | 4/2006 | Arts et al. |
| 7,540,872 B2 | 6/2009 | Schechter et al. | 2006/0079933 A1 | 4/2006 | Hushka et al. |
| 7,549,995 B2 | 6/2009 | Schultz | 2006/0084973 A1 | 4/2006 | Hushka |
| 7,553,312 B2 | 6/2009 | Tetzlaff et al. | 2006/0089670 A1 | 4/2006 | Hushka |
| 7,736,374 B2 * | 6/2010 | Vaughan et al. ............... 606/153 | 2006/0116675 A1 | 6/2006 | McClurken et al. |
| 2002/0013583 A1 | 1/2002 | Camran et al. | 2006/0129145 A1 | 6/2006 | Dycus et al. |
| 2002/0049442 A1 | 4/2002 | Roberts et al. | 2006/0167450 A1 | 7/2006 | Johnson et al. |
| 2002/0099372 A1 | 7/2002 | Schulze et al. | 2006/0167452 A1 | 7/2006 | Moses et al. |
| 2002/0107517 A1 | 8/2002 | Witt et al. | 2006/0173452 A1 | 8/2006 | Buysse et al. |
| 2002/0111624 A1 | 8/2002 | Witt et al. | 2006/0189981 A1 | 8/2006 | Dycus et al. |
| 2002/0188294 A1 | 12/2002 | Couture et al. | 2006/0190035 A1 | 8/2006 | Hushka et al. |
| 2003/0014052 A1 | 1/2003 | Buysse et al. | 2006/0217709 A1 | 9/2006 | Couture et al. |
| 2003/0014053 A1 | 1/2003 | Nguyen et al. | 2006/0229666 A1 | 10/2006 | Suzuki et al. |
| 2003/0018331 A1 | 1/2003 | Dycus et al. | 2006/0253126 A1 | 11/2006 | Bjerken et al. |
| 2003/0018332 A1 | 1/2003 | Schmaltz et al. | 2006/0259036 A1 | 11/2006 | Tetzlaff et al. |
| 2003/0032956 A1 | 2/2003 | Lands et al. | 2006/0264922 A1 | 11/2006 | Sartor et al. |
| 2003/0069570 A1 | 4/2003 | Witzel et al. | 2006/0264931 A1 | 11/2006 | Chapman et al. |
| 2003/0069571 A1 | 4/2003 | Treat et al. | 2006/0283093 A1 | 12/2006 | Petrovic et al. |
| 2003/0078578 A1 | 4/2003 | Truckai et al. | 2006/0287641 A1 | 12/2006 | Perlin |
| 2003/0109875 A1 | 6/2003 | Tetzlaff et al. | 2007/0016182 A1 | 1/2007 | Lipson et al. |
| 2003/0114851 A1 | 6/2003 | Truckai et al. | 2007/0016187 A1 | 1/2007 | Weinberg et al. |
| 2003/0139741 A1 | 7/2003 | Goble et al. | 2007/0043352 A1 | 2/2007 | Garrison et al. |
| 2003/0139742 A1 | 7/2003 | Wampler et al. | 2007/0043353 A1 | 2/2007 | Dycus et al. |

| | | | | | | |
|---|---|---|---|---|---|---|
| 2007/0060919 A1 | 3/2007 | Isaacson et al. | DE | 3612646 | | 4/1987 |
| 2007/0062017 A1 | 3/2007 | Dycus et al. | DE | 8712328 | | 3/1988 |
| 2007/0074807 A1 | 4/2007 | Guerra | DE | 4303882 | | 8/1994 |
| 2007/0078456 A1 | 4/2007 | Dumbauld et al. | DE | 4403252 | | 8/1995 |
| 2007/0078458 A1 | 4/2007 | Dumbauld et al. | DE | 19515914 | | 7/1996 |
| 2007/0078459 A1 | 4/2007 | Johnson et al. | DE | 29616210 | | 1/1997 |
| 2007/0088356 A1 | 4/2007 | Moses et al. | DE | 19608716 | | 4/1997 |
| 2007/0106295 A1 | 5/2007 | Garrison et al. | DE | 19751106 | | 5/1998 |
| 2007/0106297 A1 | 5/2007 | Dumbauld et al. | DE | 19751108 | | 5/1999 |
| 2007/0118111 A1 | 5/2007 | Weinberg | DE | 10031773 | | 11/2001 |
| 2007/0118115 A1 | 5/2007 | Artale et al. | DE | 20 2007 009 318 | | 10/2007 |
| 2007/0142833 A1 | 6/2007 | Dycus et al. | DE | 19738457 | | 1/2009 |
| 2007/0142834 A1 | 6/2007 | Dumbauld | EP | 0364216 | | 4/1990 |
| 2007/0156139 A1 | 7/2007 | Schechter et al. | EP | 0467501 | | 1/1992 |
| 2007/0156140 A1 | 7/2007 | Baily | EP | 0518230 | | 12/1992 |
| 2007/0173811 A1 | 7/2007 | Couture et al. | EP | 0541930 | | 5/1993 |
| 2007/0173814 A1 | 7/2007 | Hixson et al. | EP | 0572131 | | 12/1993 |
| 2007/0179499 A1 | 8/2007 | Garrison | EP | 0584787 | | 3/1994 |
| 2007/0198011 A1 | 8/2007 | Sugita | EP | 0589453 | | 3/1994 |
| 2007/0213712 A1 | 9/2007 | Buysse et al. | EP | 0589555 | | 3/1994 |
| 2007/0255279 A1 | 11/2007 | Buysse et al. | EP | 0623316 | | 11/1994 |
| 2007/0260235 A1 | 11/2007 | Podhajsky | EP | 0624348 | | 11/1994 |
| 2007/0260238 A1 | 11/2007 | Guerra | EP | 0650701 | | 5/1995 |
| 2007/0260241 A1 | 11/2007 | Dalla Betta et al. | EP | 0694290 | | 3/1996 |
| 2007/0260242 A1 | 11/2007 | Dycus et al. | EP | 0717966 | | 6/1996 |
| 2007/0265616 A1 | 11/2007 | Couture et al. | EP | 0754437 | | 3/1997 |
| 2008/0004616 A1 | 1/2008 | Patrick | EP | 0517243 | | 9/1997 |
| 2008/0009860 A1 | 1/2008 | Odom | EP | 0853922 | | 7/1998 |
| 2008/0015575 A1 | 1/2008 | Odom et al. | EP | 0875209 | | 11/1998 |
| 2008/0021450 A1 | 1/2008 | Couture | EP | 0878169 | | 11/1998 |
| 2008/0033428 A1 | 2/2008 | Artale et al. | EP | 0887046 | | 1/1999 |
| 2008/0039835 A1 | 2/2008 | Johnson et al. | EP | 0923907 | | 6/1999 |
| 2008/0039836 A1 | 2/2008 | Odom et al. | EP | 0986990 | | 3/2000 |
| 2008/0045947 A1 | 2/2008 | Johnson et al. | EP | 1034748 | | 9/2000 |
| 2008/0058802 A1 | 3/2008 | Couture et al. | EP | 1034748 | | 9/2000 |
| 2008/0082100 A1 | 4/2008 | Orton et al. | EP | 1025807 | | 10/2000 |
| 2008/0091189 A1 | 4/2008 | Carlton | EP | 1034746 | | 10/2000 |
| 2008/0114356 A1 | 5/2008 | Johnson et al. | EP | 1050278 | | 11/2000 |
| 2008/0167651 A1 | 7/2008 | Tetzlaff et al. | EP | 1053719 | | 11/2000 |
| 2008/0195093 A1 | 8/2008 | Couture et al. | EP | 1053720 | | 11/2000 |
| 2008/0215051 A1 | 9/2008 | Buysse et al. | EP | 1055399 | | 11/2000 |
| 2008/0243106 A1* | 10/2008 | Coe et al. ............... 606/1 | EP | 1055400 | | 11/2000 |
| 2008/0243120 A1 | 10/2008 | Lawes et al. | EP | 1080694 | | 3/2001 |
| 2008/0249527 A1 | 10/2008 | Couture | EP | 1082944 | | 3/2001 |
| 2008/0312653 A1 | 12/2008 | Arts et al. | EP | 1159926 | | 12/2001 |
| 2008/0319442 A1 | 12/2008 | Unger et al. | EP | 1177771 | | 2/2002 |
| 2009/0012520 A1 | 1/2009 | Hixson et al. | EP | 1301135 | | 4/2003 |
| 2009/0018535 A1 | 1/2009 | Schechter et al. | EP | 1330991 | | 7/2003 |
| 2009/0024126 A1 | 1/2009 | Artale et al. | EP | 1486177 | | 6/2004 |
| 2009/0043304 A1 | 2/2009 | Tetzlaff et al. | EP | 1472984 | | 11/2004 |
| 2009/0048596 A1 | 2/2009 | Shields et al. | EP | 0774232 | | 1/2005 |
| 2009/0062794 A1 | 3/2009 | Buysse et al. | EP | 1527747 | | 5/2005 |
| 2009/0082766 A1 | 3/2009 | Unger et al. | EP | 1530952 | | 5/2005 |
| 2009/0082767 A1 | 3/2009 | Unger et al. | EP | 1532932 | | 5/2005 |
| 2009/0082769 A1 | 3/2009 | Unger et al. | EP | 1535581 | | 6/2005 |
| 2009/0088738 A1 | 4/2009 | Guerra et al. | EP | 1609430 | | 12/2005 |
| 2009/0088739 A1 | 4/2009 | Hushka et al. | EP | 1632192 | | 3/2006 |
| 2009/0088740 A1 | 4/2009 | Guerra et al. | EP | 1642543 | | 4/2006 |
| 2009/0088741 A1 | 4/2009 | Hushka et al. | EP | 1645238 | | 4/2006 |
| 2009/0088744 A1 | 4/2009 | Townsend | EP | 1645240 | | 4/2006 |
| 2009/0088745 A1 | 4/2009 | Hushka et al. | EP | 1649821 | | 4/2006 |
| 2009/0088746 A1 | 4/2009 | Hushka et al. | EP | 1707143 | | 10/2006 |
| 2009/0088747 A1 | 4/2009 | Hushka et al. | EP | 1769765 | | 4/2007 |
| 2009/0088748 A1 | 4/2009 | Guerra et al. | EP | 1769766 | | 4/2007 |
| 2009/0088749 A1 | 4/2009 | Hushka et al. | EP | 1929970 | | 6/2008 |
| 2009/0088750 A1 | 4/2009 | Hushka et al. | EP | 1683496 | | 12/2008 |
| 2009/0112206 A1 | 4/2009 | Dumbauld et al. | GB | 623316 | | 5/1949 |
| 2009/0131934 A1 | 5/2009 | Odom et al. | GB | 1490585 | | 11/1977 |
| 2009/0149853 A1 | 6/2009 | Shields et al. | GB | 2214430 | A | 6/1989 |
| 2009/0149854 A1 | 6/2009 | Cunningham et al. | GB | 2213416 | A | 8/1989 |
| 2009/0171350 A1 | 7/2009 | Dycus et al. | JP | 61-501068 | | 9/1984 |
| 2009/0171353 A1 | 7/2009 | Johnson et al. | JP | 65-502328 | | 3/1992 |
| 2009/0182327 A1 | 7/2009 | Unger | JP | 5-5106 | | 1/1993 |
| 2009/0187188 A1 | 7/2009 | Guerra et al. | JP | 5-40112 | | 2/1993 |
| | | | JP | 06343644 | A2 | 12/1994 |
| FOREIGN PATENT DOCUMENTS | | | JP | 07265328 | A2 | 10/1995 |
| DE | 2415263 | 10/1975 | JP | 08056955 | A2 | 3/1996 |
| DE | 2514501 | 10/1976 | JP | 08252263 | A2 | 10/1996 |
| DE | 2627679 | 1/1977 | JP | 09010223 | A2 | 1/1997 |

| | | |
|---|---|---|
| JP | 11244298 A2 | 9/1999 |
| JP | 2000-342599 A2 | 12/2000 |
| JP | 2000-350732 A2 | 12/2000 |
| JP | 2001-008944 A2 | 1/2001 |
| JP | 2001-029356 A2 | 2/2001 |
| JP | 2001-128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/022056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 08/045348 | 4/2008 |
| WO | WO 08/045350 | 4/2008 |
| WO | WO 2008/045348 | 4/2008 |
| WO | WO 2008/045350 | 4/2008 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectomy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, July 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98957771 dated Aug. 9, 2001.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05019429.9 dated May 6, 2008.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008515.6 dated Jan. 8, 2009.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 014016 dated Jan. 28, 2008.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 07 021646.3 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l-Search Report PCT/US08/61498 dated Sep. 22, 2008.
Int'l,Search Report EP 05019429.9 dated May 6, 2008.
Int'l. Search Report EP 07 014016 dated Jan. 28, 2008.
Int'l Search Report EP 07 021646.0 dated Jul. 9, 2008.
Int'l. Search Report EP 08 02692.5 dated Dec. 12, 2008.
Int'l Search Report EP 09 152267.2 Dated Jun. 15, 2009.
Int'l Search Report EP 09 152898.4 Dated Jun. 10, 2009.
Int'l Search Report PCT/US08/61498 dated Sep. 22, 2008.
Int'l Search Report PCT/US09/032690 dated Jun. 16, 2009.
European Search Report 11185028.5 dated Jan. 2, 2012.

* cited by examiner

METHOD OF TRANSFERRING PRESSURE IN AN ARTICULATING SURGICAL INSTRUMENT

BACKGROUND

1. Technical Field

The present disclosure relates to an apparatus for remotely activating jaw members on an articulating surgical instrument. In particular, the apparatus provides an end effector capable of transferring a sufficient force to the jaw members to cause a therapeutic effect on tissue clamped between the jaw members.

2. Background of Related Art

Typically in a laparoscopic, an endoscopic, or other minimally invasive surgical procedure, a small incision or puncture is made in a patient's body. A cannula is then inserted into a body cavity through the incision, which provides a passageway for inserting various surgical devices such as scissors, dissectors, retractors, or similar instruments. To facilitate operability through the cannula, instruments adapted for laparoscopic surgery typically include a relatively narrow shaft supporting an end effector at its distal end and a handle at its proximal end. Arranging the shaft of such an instrument through the cannula allows a surgeon to manipulate the proximal handle from outside the body to cause the distal end effector to carry out a surgical procedure at a remote internal surgical site. This type of laparoscopic procedure has proven beneficial over traditional open surgery due to reduced trauma, improved healing and other attendant advantages.

An articulating laparoscopic or endoscopic instrument may provide a surgeon with a range of operability suitable for a particular surgical procedure. The instrument may be configured such that the end effector may be aligned with an axis of the instrument to facilitate insertion through a cannula, and thereafter, the end effector may be caused to articulate, pivot or move off-axis as necessary to appropriately engage tissue. When the end effector of an articulating instrument comprises a pair of jaw members for grasping tissue, a force transmission mechanism such as a flexible control wire may be provided to open or close the jaws. For example, the control wire may extend through an outer shaft from the handle to the jaws such that the surgeon may create a tension in the control wire to cause the jaws to move closer to one another. The closure or clamping force generated in the jaws may be directly related to the tension in the control wire applied by the surgeon.

One type of laparoscopic or endoscopic instrument is intended to generate a significant closure force between jaw members to seal small diameter blood vessels, vascular bundles or any two layers of tissue with the application electrosurgical or RF energy. The two layers may be grasped and clamped together by the jaws of an electrosurgical forceps, and an appropriate amount of electrosurgical energy may be applied through the jaws. In this way, the two layers of tissue may be fused together. The closure forces typically generated by this type of procedure may present difficulties when using a typical control wire to open and close the jaws of an articulating instrument.

For example, a surgeon's efforts to position the jaws may be frustrated by a tendency for a control wire under tension to realign the jaws with the axis of the instrument after the jaws have been articulated off-axis. Although this tendency may be observed in any type of articulating instrument, the tendency is particularly apparent when the closure forces and necessary tension in the control wire are relatively high, as is common in an electrosurgical sealing instrument. This tendency may be created by the direction of reaction forces through the outer shaft of the instrument.

SUMMARY

The present disclosure describes an end effector for incorporation into an articulating surgical instrument, which decouples a force application mechanism from an outer shaft of the instrument. The end effector includes a fixed bearing member, which defines an end effector axis and provides mounting surfaces for attachment to a distal end of the surgical instrument. The end effector also includes at least one jaw member that is configured to move relative to an opposing jaw member between an open configuration and a closed configuration. A force transfer member is configured for longitudinal motion with respect to the fixed bearing member and includes a pivot channel therein. The end effector also includes a reactive member coupled between the fixed bearing member and the at least one jaw member. The reactive member is constructed from a thin strip of conformable material and extends through the pivot channel such that relative longitudinal motion between the fixed bearing member and the force transfer member causes the reactive member to flex and the at least one jaw member to move relative to the opposing jaw.

The conformable material from which the reactive member is constructed may comprise spring steel or a shape memory alloy.

The force transfer member may be configured to abut the at least one jaw member when the at least one jaw member is in the closed configuration to generate a substantial clamping force. The force transfer member may also exhibit a forked configuration.

The end effector may also include a motion conversion mechanism operatively associated with the force transfer member to urge the force transfer member longitudinally. The motion conversion mechanism may include an input shaft configured for rotational movement relative to the fixed bearing member, and the input shaft may be further configured for connection to a torsion cable or rod to receive rotational motion therefrom. The input shaft may support a power screw and the force transfer member may be coupled to a translation nut such that the force transfer member translates longitudinally upon rotational motion in the power screw.

The reactive member of the end effector may be coupled to the at least one jaw member such that distal translation of the reactive member moves the at least one jaw member to the closed configuration, and proximal translation of the reactive member moves the at least one jaw member to the open configuration. The at least one jaw member may include a pair of moveable jaws, or the end effector may include an opposing jaw member that is stationary relative to the fixed bearing member.

According to another aspect of the disclosure, a surgical instrument includes a handle portion near a proximal end of the surgical instrument adapted for manipulation by a user to control the surgical instrument, a tubular shaft extending distally from the handle portion and defining an instrument axis, and an end effector pivotally coupled to a distal end of the tubular shaft such that the end effector may articulate relative to the instrument axis. The end effector defines an end effector axis and includes a pair of jaw members configured to pivot about a pivot axis that is transverse to the end effector axis to move between an open and a closed configuration. The end effector also includes a force transfer member configured for longitudinal motion with respect to a fixed bearing member. The force transfer member includes a pivot channel therein. A reactive member of the end effector is coupled between the fixed bearing member and the at least one jaw member. The reactive member is constructed from a thin strip of conformable material and extends through the pivot channel such that relative longitudinal motion between the fixed bearing member and the force transfer member causes the reactive member to flex and the at least one jaw member to move relative to the opposing jaw.

The end effector of the surgical instrument may further include a motion conversion mechanism for converting rotational motion to longitudinal motion that is operatively associated with the force transfer member to urge the force transfer member longitudinally. Also, a torsion cable or rod may be coupled to the end effector to deliver rotational motion thereto.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1A:
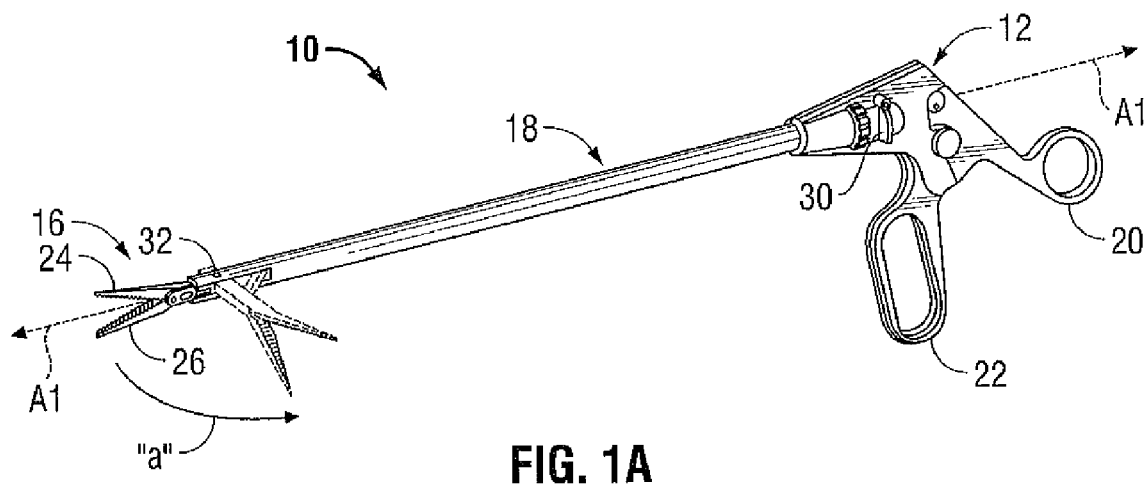
FIG. 1A is a perspective view of an articulating laparoscopic surgical instrument that may incorporate the features of the present disclosure.

Referring initially to FIG. 1A, an articulating endoscopic instrument is depicted generally as 10. The instrument 10 includes a handle portion 12 near a proximal end, an end effector 16 near a distal end and an elongated shaft 18 therebetween. Elongated shaft 18 defines an instrument axis "A1" to which end effector 16 aligns for insertion through a cannula (not shown) or other suitable introducer. End effector 16 is articulatable off-axis (as indicated in phantom) to appropriately engage tissue. Handle portion 12 is manipulatable by the surgeon from outside a body cavity to control the movement of the end effector 16 positioned inside the body at a tissue site. For example, the surgeon may separate and approximate a pivoting handle 20 relative to a stationary handle 22 to respectively open and close jaw members 24, 26. Also, a surgeon may pivot lever 30 to cause the end effector 16 to articulate or pivot in a horizontal plane about a pivot pin 32. A more complete description of the components and operation of instrument 10 may be found in U.S. Patent Application Publication No. 2006/0025907 to Nicholas et al.

Figure 1B:
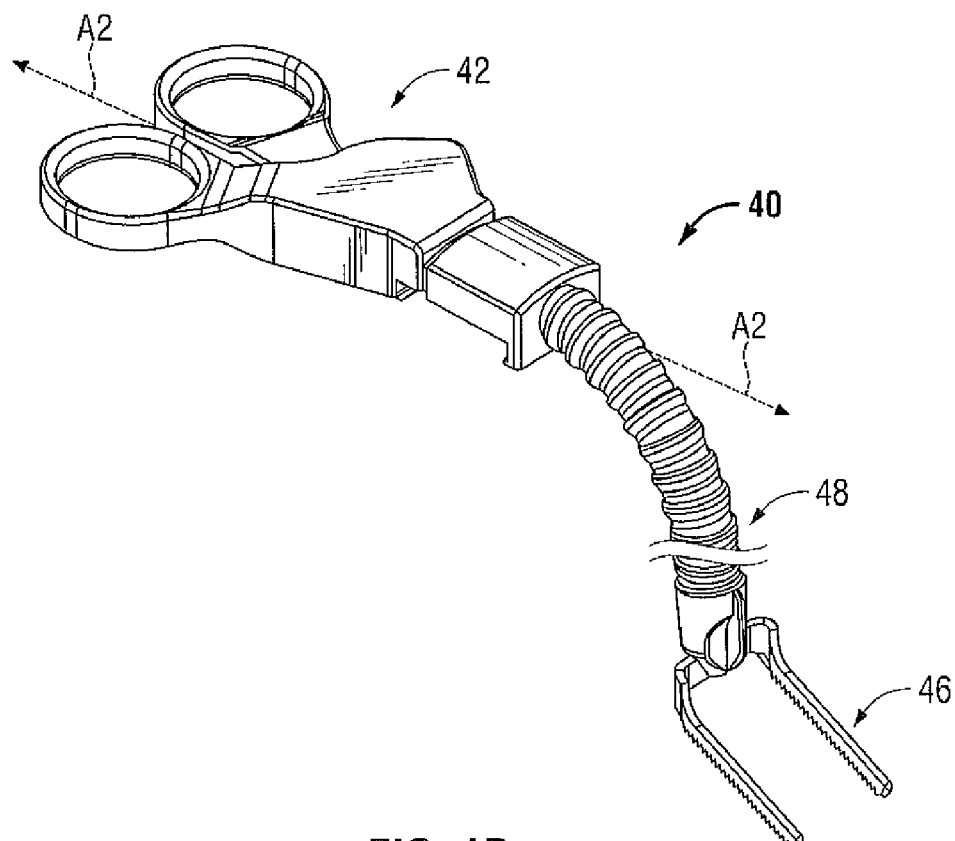
FIG. 1B is a perspective view of an embodiment of an articulating surgical instrument according to one embodiment of the present disclosure.

Another type of known articulating surgical instrument is depicted generally as 40 in FIG. 1B. Instrument 40 includes a handle portion 42 that is manipulatabe to control the movement of end effector 46. Handle portion 42 is coupled to end effector 46 through a flexible shaft 48 that moves into and out of alignment with instrument axis "A2."

Both articulating instruments 10, 40 provide for off-axis operation of the respective end effectors 16, 46. Both instruments 10, 40 may exhibit a tendency to align themselves to the respective instrument axes A1, A2 when the end effectors 16, 46 are operated if the instruments 10, 40 are equipped with a force transmission mechanism that generates reaction forces in outer shafts 18, 48. Accordingly, an end effector 100 as described below may be incorporated into instruments similar to instruments 10, 40 to decouple any reactionary forces from outer shafts of the instruments. End effectors in accordance with the present disclosure may also be incorporated into a non-articulating instrument.

Figure 2A:
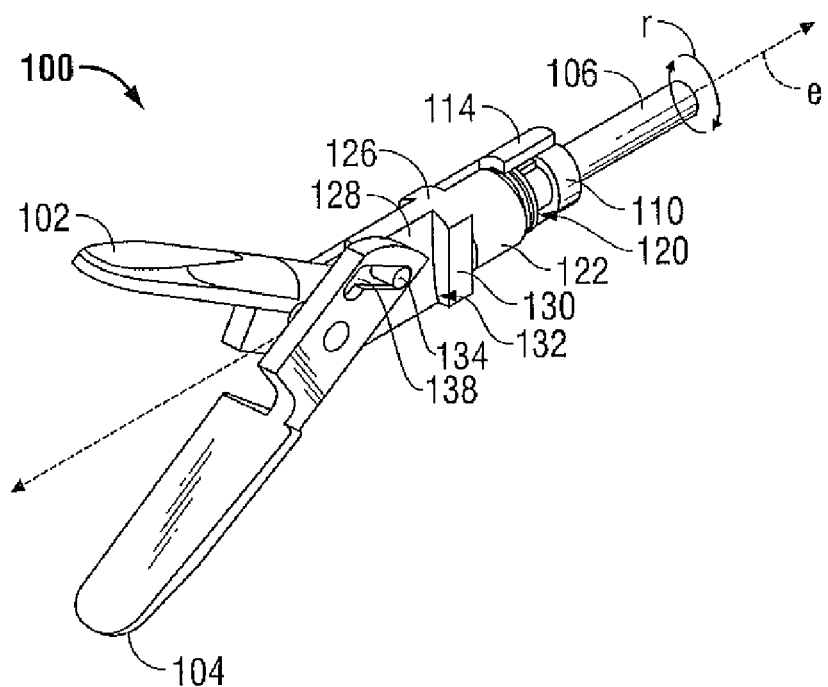
FIG. 2A is a perspective view of an end effector in accordance with an embodiment of the present disclosure in an open configuration.

Referring now to FIGS. 2A through 5B, an end effector in accordance with the present disclosure is depicted generally as 100. End effector 100 includes jaw members 102 and 104 that are selectively movable between an open configuration as seen in FIG. 2A and a closed configuration as depicted in FIG. 2B. This motion of the jaw members 102, 104 is achieved upon the application of a torsion force to end effector 100. Therefore, a control wire placed in tension, which as discussed above may generate reactionary forces in the outer shaft of an instrument and tend to frustrate the articulation of the instrument, is not necessary.

End effector 100 is adapted to receive a torsion force through input shaft 106 such that input shaft 106 may rotate about an end effector axis "e" as indicated by arrows "r." Input shaft 106 includes a bore 108 (FIG. 3), which provides connectivity to a suitable external source of rotational motion (not shown). The rotational motion may be generated, for example, by an electric motor, or alternatively by a surgeon using a manual control surface at a handle portion of the instrument. If the rotational motion is generated in a handle portion of the instrument, a flexible torsion cable 109 (shown in phantom in FIG. 3) may be positioned through the instrument shaft to transmit rotational motion from the handle to the end effector 100.

Figure 3:
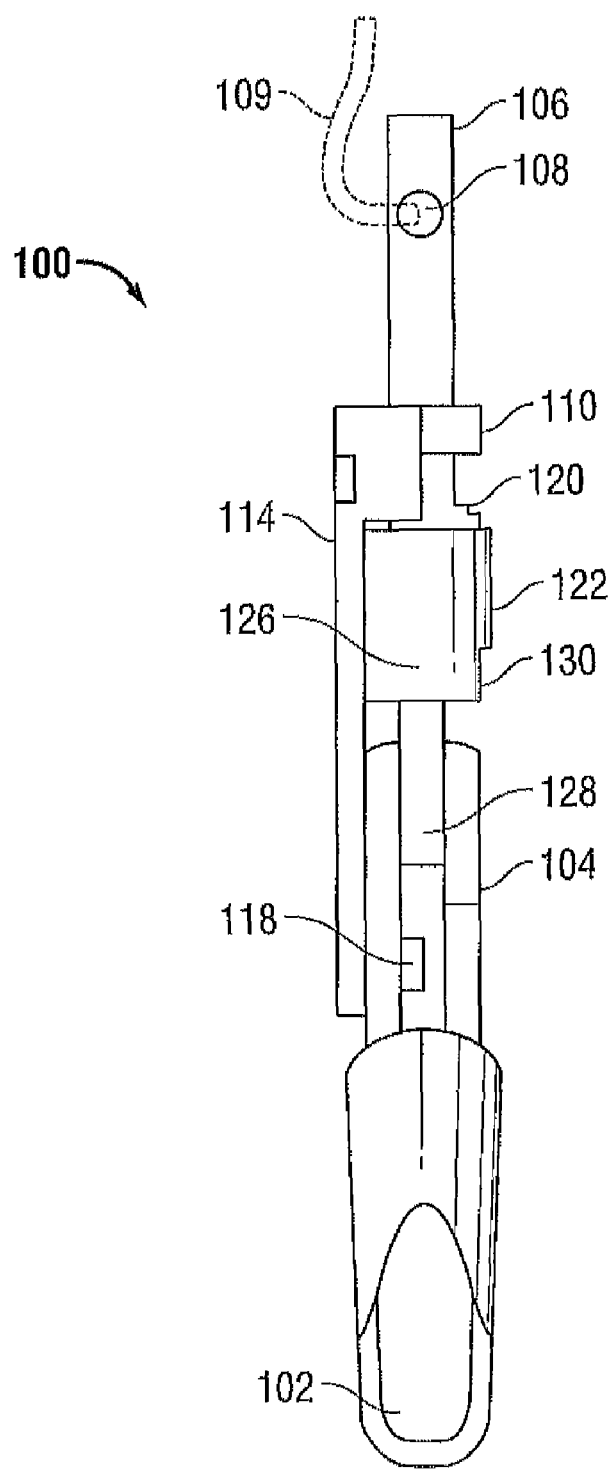
FIG. 3 is a top view of the end effector of FIG. 2A in the open configuration.

Input shaft 106 rotates inside a fixed bearing member 110. Fixed bearing member 110 provides mounting surfaces for direct or indirect fixed coupling to an articulating distal end of an instrument shaft, which remains stationary relative thereto. In this way, the entire end effector 100 is supported by the instrument and may be caused to articulate relative to an instrument axis. Fixed bearing member 110 also supports a reactive member 114 on an outer surface thereof. As best seen in FIG. 3, reactive member 114 extends distally from fixed bearing member 110 and comprises a pivot boss 118 (FIG. 3) extending into jaw member 102. Jaw member 102 is pivotable about pivot boss 118 as the end effector 100 is moved between the open and closed configurations. Although removed from the figures for clarity, an additional reactive member 114 is supported by fixed bearing member 110 so as to mirror the reactive member 114 shown and provide a pivot boss 118 about which jaw member 104 may rotate when end effector 100 is moved between the open and closed configurations. Reactive member 114 remains stationary relative to fixed bearing member 110 as jaw members 102, 104 pivot open and closed.

A power screw 120 is supported at a distal end of input shaft 106. The power screw 120 is coupled to the input shaft 106 such that both the power screw 120 and the input shaft 106 rotate together. Rotation of the power screw 120 drives a translation nut 122 longitudinally along end effector axis "e." For example, rotation of power screw 120 in a first direction advances translation nut 122 from the position depicted in FIG. 4A where the translation nut is disposed at a distance "d" from the fixed bearing member 110, to the position depicted in FIG. 4B where the translation nut 122 is a greater distance "D" from the fixed bearing member 110. Likewise, rotation of power screw 120 in an opposite direction withdraws translation nut 122 such that translation nut 122 becomes closer to the fixed bearing member 110.

A force transfer member 126 is supported at a distal end of translation nut 122. Force transfer member 126 may be coupled to translation nut 122 or may be formed integrally therewith such that the force transfer member 126 translates along with the translation nut 122. Force transfer member 126 is formed with a central web 128 having a pair of proximal flanges 130 extending therefrom in opposite directions. The proximal flanges 130 exhibit sloped base portions 132 at their lower ends. An opposed pair of cam pins 134 also protrudes from central web 128.

The cam pins 134 work in conjunction with proximal flanges 130 to open and close the jaw members 102, 104. Cain pins 134 engage a pair of cam slots 138 on the jaw members 102, 104 as the cam pins 134 translate distally along with force transfer member 126. Distal translation of cam pins 134 through cam slots 138 cause the jaw members 102, 104 to move from the open configuration of FIG. 4A to the nearly-closed configuration of FIG. 5A. In the nearly-closed configuration, the sloped base portions 132 of the proximal flanges 130 contact proximal faces of jaw members 102, 104. Also at the nearly closed configuration, each of the cam pins 134 reach a curve 144 in the respective cam slots 138 that allows force to be transferred from the cam pins 134 to the proximal flanges 130 of the force transfer member 126. Further distal translation of the force transfer member 126 will move the jaws from the nearly-closed configuration of FIG. 5A to the closed configuration of FIG. 5B as the sloped base portions 132 press against the proximal faces of the jaw members 102, 104.

Figure 2B:
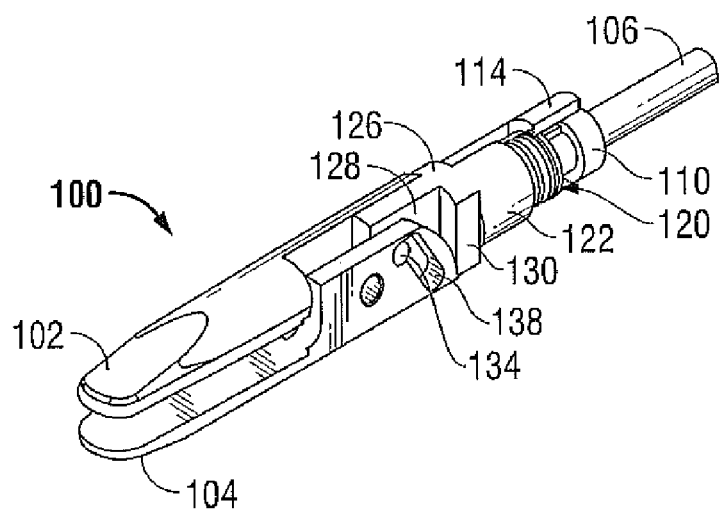
FIG. 2B is a perspective view of the end effector of FIG. 2A in a closed configuration.
Figure 4A:
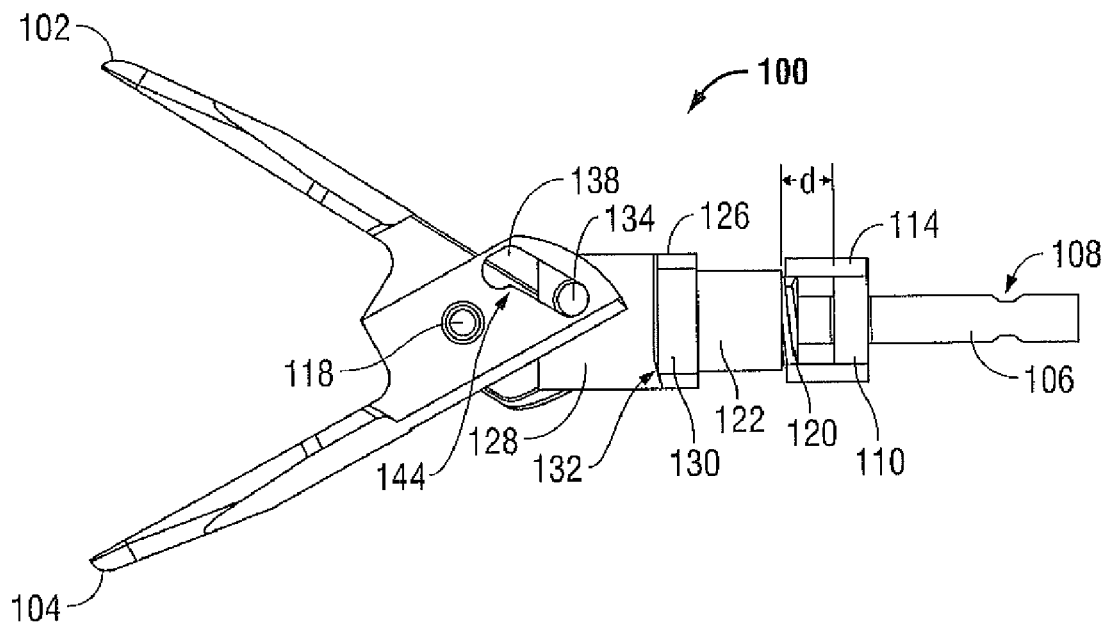
FIG. 4A is a side view of the end effector of FIG. 2A in the open configuration.
Figure 4B:
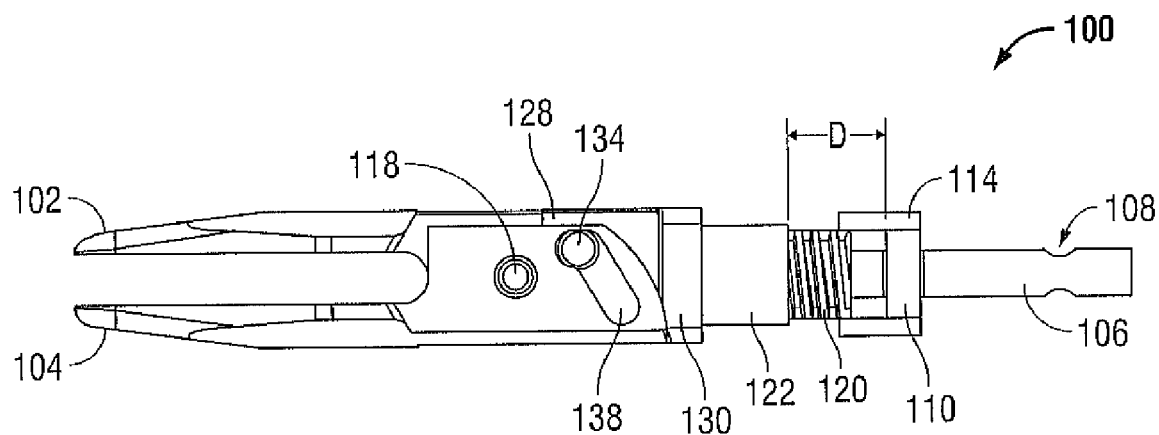
FIG. 4B is a side view of the end effector of FIG. 2A in the closed configuration.
Figure 5A:
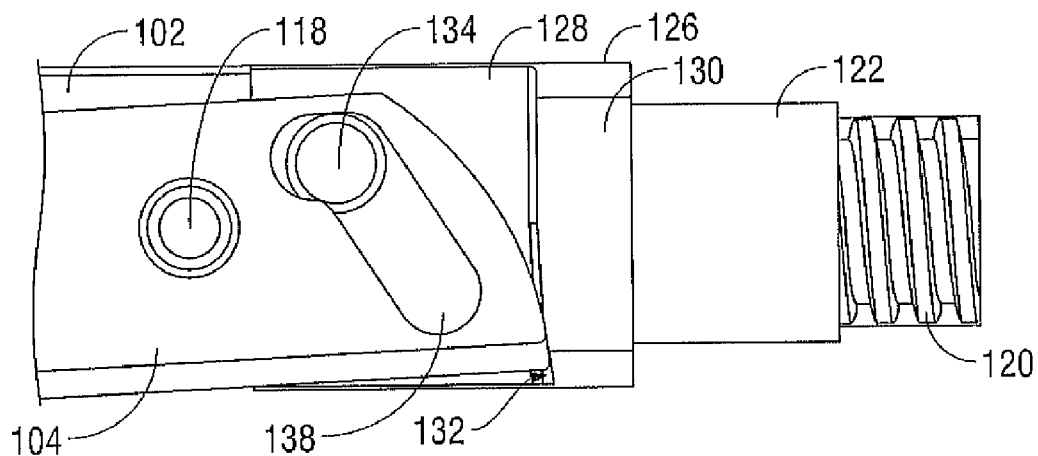
FIG. 5A is an enlarged, side view of a pivoting portion of the end effector of FIG. 2A in a nearly closed configuration.
Figure 5B:
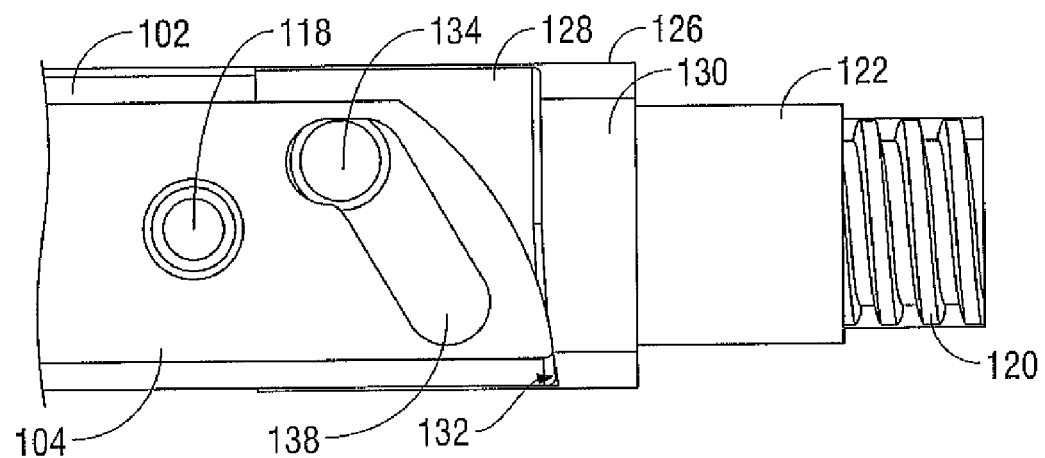
FIG. 5B is an enlarged, side view of the pivoting portion of the end effector of FIG. 2A in the closed configuration.

In the closed configuration of FIGS. 2B, 4B and 5B, the jaw members 102, 104 may generate a significant clamping force that can be directed at tissue positioned between the jaw members 102, 104. As the proximal flanges 130 press distally against the jaw members 102, 104, the jaw members 102, 104 press distally on the pivot bosses 118 of reactive member 114. An opposite reaction force is realized as a tensile force in the reactive member 114, which links the jaw members to the fixed bearing member 110. Because the reaction force is contained entirely within the end effector 100, this arrangement allows an articulating instrument to which the end effector 100 is attached to close jaw members 102, 104 without creating a tendency for the end effector to conform to an axis of the instrument.

Figure 6A:
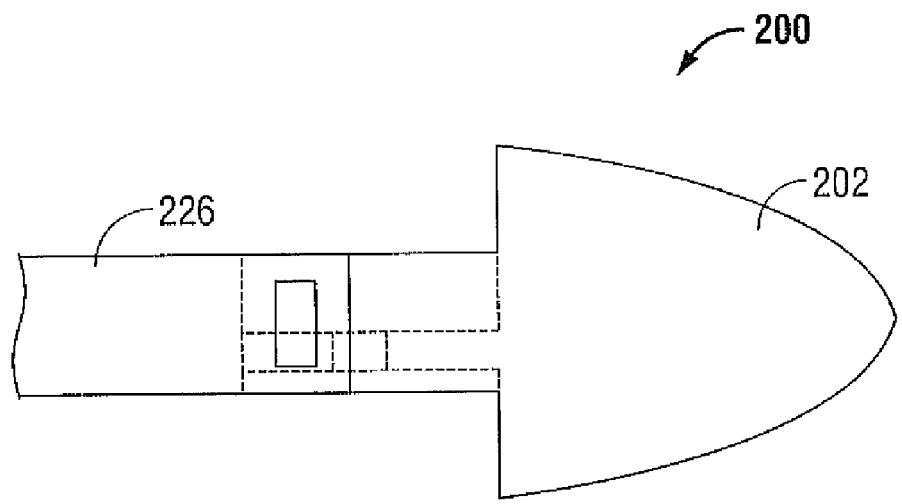
FIG. 6A is a partial top view of an alternate embodiment of an end effector in accordance with the present disclosure.
Figure 6B:
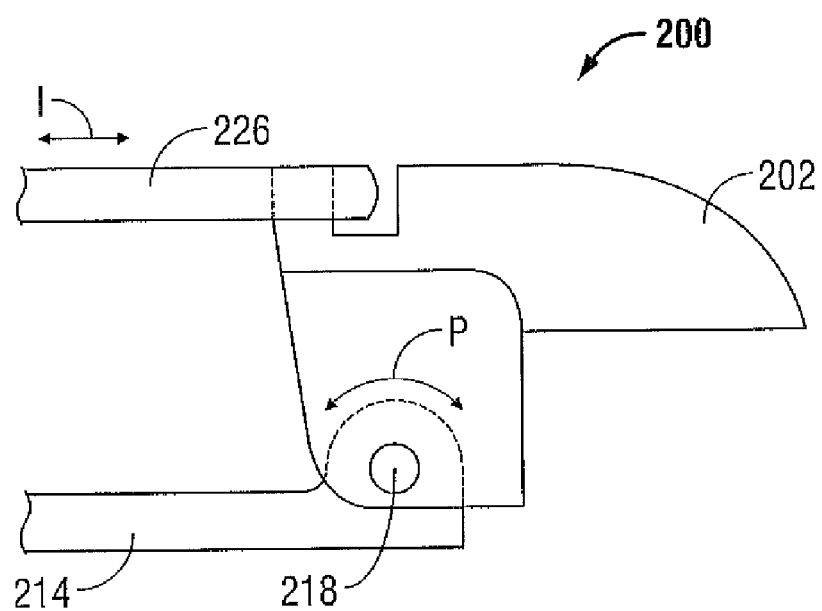
FIG. 6B is a side view of the end effector of FIG. 6A.

Referring now to FIGS. 6A and 6B, an alternate embodiment of an end effector in accordance with the present disclosure is depicted generally as 200. End effector 200 defines a lever cam arrangement and comprises a jaw member 202, a reactive member 214, which supports a pivot boss 218, and a force transfer member 226. Jaw member 202 is configured to pivot about pivot boss 218 (as indicated by arrows "p") in response to longitudinal translation (as indicated by arrows "l") of the force transfer member 226 at some lateral distance from the pivot boss 218. End effector 200 may be equipped with an opposing jaw member (not shown), stationary or moveable, such that jaw member 202 is moved between an open and closed configuration as it pivots about pivot boss 218. The force transfer member 226 is coupled to the jaw member 202 such that distal translation of the force transfer member 226 moves jaw member 202 to the closed configuration, and proximal translation of the force transfer member 226 moves jaw member 202 to the open configuration.

Reactive member 214 is supported at a proximal end by a fixed member (not shown) as part of a motion conversion mechanism that converts rotational motion to longitudinal motion. For example, a motion conversion mechanism may include an arrangement of a power screw and translation nut as described above. Alternatively, a worm gear arrangement may be configured to drive force transfer member 226 longitudinally relative to reactive member 214. This arrangement would also allow reactive member 214 to carry reactive forces entirely within the end effector 200. Reactive member 214, however, would be placed in compression as jaw member 202 is moved to the closed configuration.

Figure 7A:
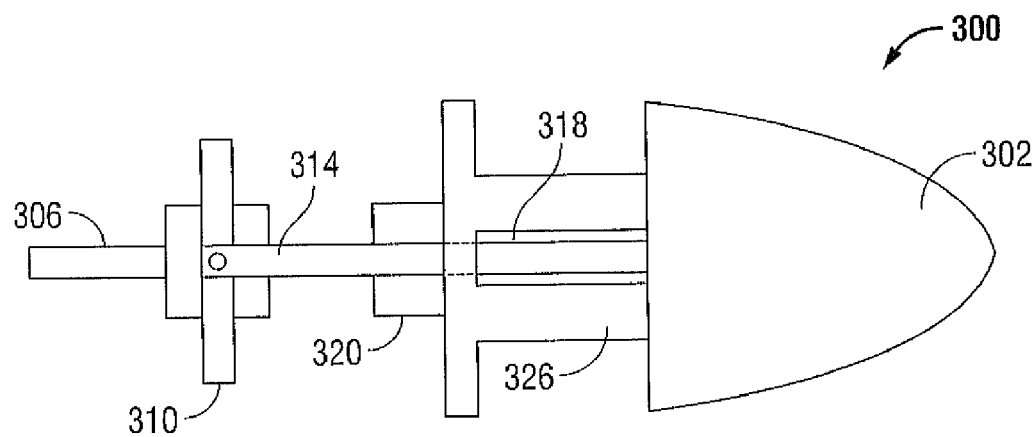
FIG. 7A is a top view of another alternate embodiment of an end effector in accordance with the present disclosure.
Figure 7B:
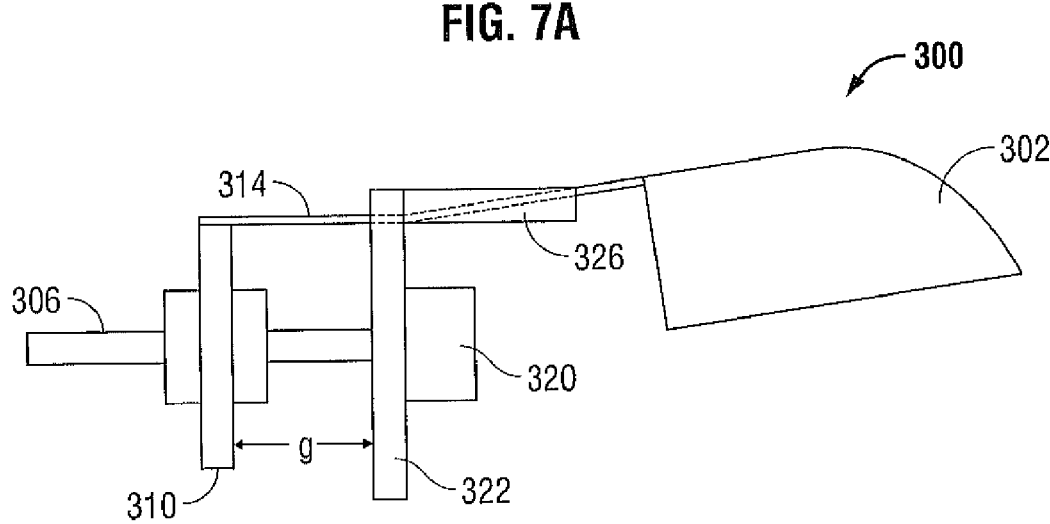
FIG. 7B is a side view of the end effector of FIG. 7A in an open configuration.
Figure 7C:
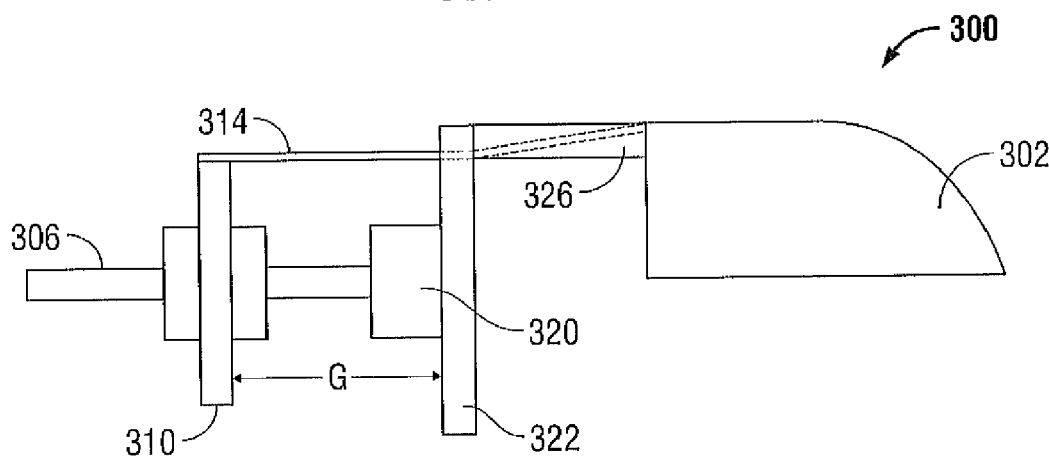
FIG. 7C is a side view of the end effector of FIG. 7A in a closed configuration.

Referring now to FIGS. 7A through 7C, another alternate embodiment of an end effector in accordance with the present disclosure is depicted generally as 300. End effector 300 includes a jaw member 302, which is movable between an open configuration and a closed configuration as described below. End effector 300 is adapted to receive a torsion force from an external source through input shaft 306. Input shaft 306 rotates inside a fixed bearing member 310. Fixed bearing member 310 is coupled to an articulating distal end of an instrument shaft and remains stationary relative thereto. In this way, the entire end effector 300 is supported by the instrument and may be caused to articulate relative to an instrument axis.

Fixed bearing member 310 also supports a reactive member 314 on an upper surface thereof. Reactive member 314 is formed from a thin strip of conformable material such as spring steel or a shape memory alloy, and extends distally from fixed bearing member 310 to jaw member 302 through a pivot channel 318. Longitudinal motion of the reactive member 314 through the pivot channel 318, e.g., relative longitudinal motion between the reactive member 314 and the pivot channel 318 caused by longitudinal motion of the force transfer member 326, causes reactive member 314 to flex in an upward or downward direction to move jaw member 302 between an open configuration as depicted in FIG. 7B and a closed configuration as depicted in FIG. 7C.

A power screw 320 is supported at a distal end of input shaft 306 such that both the power screw 320 and the input shaft 306 may rotate together. Rotation of the power screw 320 drives a translation nut 322 longitudinally with respect to fixed bearing member 310. For example, rotation of power screw 320 in a first direction advances translation nut 322 from the position depicted in FIG. 7B where a gap "g" separates translation nut 322 from fixed bearing member 310, to the position depicted in FIG. 7C where a larger gap "G" separates translation nut 322 from fixed bearing member 310. Likewise, rotation of power screw 320 in an opposite direction withdraws translation nut 322 such that it becomes closer to the fixed bearing member 310.

A force transfer member 326 is supported at an upper end of translation nut 322. Force transfer member 326 may be coupled to translation nut 322 or formed integrally therewith such that the force transfer member 326 translates along with translation nut 322. Pivot channel 318 is extends entirely through force transfer member 326 at a distal end such that force transfer member 326 exhibits a forked configuration as best seen in FIG. 7A. When end effector 300 is in the closed configuration depicted in FIG. 7C, a distal end of the forked force transfer member 326 contacts a proximal face of the jaw member 302. This allows force to be transferred from the reactive member 314 to the force transfer member 326. Further distal translation of the translation nut 322 will result in force transfer member 326 pressing against the proximal face of the jaw member 302 such that jaw member 302 may generate a substantial clamping force. When the force transfer member 326 presses against the jaw member 302, a reaction force is realized as a tensile force in the reactive member 314. Since the reaction force is contained within the end effector 300, the closure of jaw member 302 does not tend to frustrate the articulation of an instrument to which end effector 300 is coupled.

Although the foregoing disclosure has been described in some detail by way of illustration and example, for purposes of clarity or understanding, it will be obvious that certain changes and modifications may be practiced within the scope of the appended claims.

What is claimed is:

1. An end effector for a surgical instrument, comprising:
   a fixed bearing member defining a longitudinal axis and providing mounting surfaces for attachment to a distal end of the surgical instrument;
   at least one jaw member configured to move relative to an opposing jaw member between an open configuration and a closed configuration;
   a force transfer member configured for longitudinal motion with respect to the fixed bearing member, the force transfer member including a pivot channel therein; and
   a reactive member coupled between the fixed bearing member and the at least one jaw member, the reactive member extending through the pivot channel such that the reactive member bends at a proximal end of the pivot channel, and wherein relative longitudinal motion between the fixed bearing member and the force transfer member causes the proximal end of the pivot channel to translate along the reactive member such that the at least one jaw member is induced to move relative to the opposing jaw.

2. The end effector according to claim 1, wherein the conformable material comprises spring steel or a shape memory alloy.

3. The end effector according to claim 1, wherein the force transfer member is configured to abut the at least one jaw member when the at least one jaw member is in the closed configuration to generate a substantial clamping force.

4. The end effector according to claim 3, wherein the force transfer member exhibits a forked configuration.

5. The end effector according to claim 1, further comprising a motion conversion mechanism operatively associated with the force transfer member to urge the force transfer member longitudinally.

6. The end effector according to claim 5, wherein the motion conversion mechanism includes an input shaft configured for rotational movement relative to the fixed bearing member, the input shaft further configured for connection to a torsion member to receive rotational motion therefrom.

7. The end effector according to claim 6, wherein the input shaft supports a power screw and the force transfer member is coupled to a translation nut such that the force transfer member translates longitudinally upon rotational motion in the power screw.

8. The end effector according to claim 1, wherein the reactive member is coupled to the at least one jaw member such that distal translation of the reactive member moves the at least one jaw member to the closed configuration, and proximal translation of the reactive member moves the at least one jaw member to the open configuration.

9. The end effector according to claim 1, wherein the at least one jaw member includes a pair of moveable jaws.

10. The end effector according to claim 1, wherein the opposing jaw member is stationary relative to the fixed bearing member.

11. A surgical instrument comprising:
    a handle portion near a proximal end of the surgical instrument adapted for manipulation by a user to control the surgical instrument;
    a tubular shaft extending distally from the handle portion and defining an instrument axis; and
    an end effector pivotally coupled to a distal end of the tubular shaft such that the end effector may articulate relative to the instrument axis, the end effector defining an end effector axis and comprising:
    a pair of jaw members configured to pivot about a pivot axis to move between an open and a closed configuration, the pivot axis transverse to the end effector axis;
    a force transfer member configured for longitudinal motion with respect to a fixed bearing member, the force transfer member including a pivot channel therein; and
    a reactive member coupled between the fixed bearing member and the at least one jaw member, the reactive member extending through the pivot channel such that the reactive member bends at a proximal end of the pivot channel, and wherein relative longitudinal motion between the fixed bearing member and the force transfer member causes the proximal end of the pivot channel to translate along the reactive member such that the at least one jaw member is induced to move relative to the opposing jaw.

12. The surgical instrument according to claim 11, wherein the end effector further comprises a motion conversion mechanism for converting rotational motion to longitudinal motion, the motion conversion mechanism operatively associated with the force transfer member to urge the force transfer member longitudinally.

13. The surgical instrument according to claim 12, further comprising a torsion member coupled to end effector to deliver rotational motion thereto.

14. The end effector according to claim 1, wherein the reactive member is constrained by the force transfer member at a longitudinal location immediately proximal to the pivot channel.

15. The end effector according to claim 3, wherein the force transfer member is configured to press against a proximal face of the at least one jaw member when the at least one jaw member is in the closed configuration.

* * * * *